(12) United States Patent  (10) Patent No.: US 7,923,249 B2
Rise et al.                 (45) Date of Patent:     Apr. 12, 2011

(54) AERATED LIQUID PRIMING OF CONIFER SOMATIC GERMINANTS

(75) Inventors: Marlies Rise, Milwaukee, WI (US);
    Steven Charles Grossnickle, North Saanich (CA); Shihe Fan, Edmonton (CA); Stephen Attree, Victoria (CA); Plamen Denchev, Victoria (CA); Patricia Marietta Krol, Victoria (CA); Ming Shang, Victoria (CA)

(73) Assignee: Cellfor Inc., Saanichton, British Columbia (CA)

( * ) Notice: Subject to any disclaimer, the term of this patent is extended or adjusted under 35 U.S.C. 154(b) by 0 days.

(21) Appl. No.: 11/372,172

(22) Filed: Mar. 10, 2006

(65) Prior Publication Data

US 2007/0016972 A1    Jan. 18, 2007

Related U.S. Application Data

(60) Provisional application No. 60/659,900, filed on Mar. 10, 2005.

(51) Int. Cl.
    *C12N 5/00*    (2006.01)
    *C12N 5/02*    (2006.01)

(52) U.S. Cl. .................... 435/422; 435/420; 435/430

(58) Field of Classification Search ............. 435/422, 435/420, 430
    See application file for complete search history.

(56) References Cited

U.S. PATENT DOCUMENTS

| 4,562,663 | A | 1/1986 | Redenbaugh | 800/295 |
| 4,777,762 | A | 10/1988 | Redenbaugh et al. | 47/57.6 |
| 4,957,866 | A * | 9/1990 | Gupta et al. | 435/422 |
| 5,010,685 | A | 4/1991 | Sakamoto et al. | 47/57.6 |
| 5,119,588 | A | 6/1992 | Timmis et al. | 47/58.1 R |
| 5,183,757 | A | 2/1993 | Roberts | 435/422 |
| 5,236,469 | A | 8/1993 | Carlson et al. | 47/57.6 |
| 5,294,549 | A | 3/1994 | Pullman et al. | 435/422 |
| 5,413,930 | A | 5/1995 | Becwar et al. | 435/422 |
| 5,427,593 | A | 6/1995 | Carlson et al. | 47/57.6 |
| 5,451,241 | A | 9/1995 | Cartson et al. | 47/57.6 |
| 5,464,769 | A | 11/1995 | Attree et al. | 800/319 |
| 5,482,857 | A | 1/1996 | Gupta et al. | 435/422 |
| 5,486,218 | A | 1/1996 | Carlson et al. | 47/57.6 |
| 5,491,090 | A * | 2/1996 | Handley et al. | 435/422 |

(Continued)

FOREIGN PATENT DOCUMENTS

CA    2309258    6/1999

(Continued)

OTHER PUBLICATIONS

Tautorus et al. "Bioreactor culture of *Picea mariana* Mill. (black spruce) and the species complex *Picea glauca-engelmannii* (interior spruce) somatic embryos. Growth parameters," Appl. Microbiol. Biotechnol (1992) 38:46-51.*

(Continued)

*Primary Examiner* — Susan B McCormick Ewoldt

(57) ABSTRACT

A process of priming mature, imbibed, germinated somatic embryos of a conifer species. The process comprises fully immersing mature, imbibed, germinated somatic conifer embryos in a sterile liquid nutrient medium, bubbling an oxygen-containing gas through the liquid nutrient medium containing the germinants to form an aerated embryo-containing nutrient medium, optionally exposing the aerated germinant-containing nutrient medium to light, at least intermittently, continuing the immersion, bubbling and optional exposure to light for a period of time effective to produce at least some successfully primed conifer germinants that are adapted for subsequent planting and conversion to viable seedlings, and removing the successfully primed conifer germinants from the nutrient medium.

20 Claims, 4 Drawing Sheets

U.S. PATENT DOCUMENTS

| | | | | |
|---|---|---|---|---|
| 5,506,136 | A | | 4/1996 | Becwar et al. .............. 435/422 |
| 5,558,984 | A | * | 9/1996 | Young et al. ..................... 435/3 |
| 5,965,438 | A | * | 10/1999 | Kadkade et al. ............. 435/420 |
| 6,134,830 | A | * | 10/2000 | Welty ......................... 47/58.1 R |
| 6,200,809 | B1 | | 3/2001 | Klimaszewska et al. ..... 435/422 |
| 6,245,555 | B1 | | 6/2001 | Curtis .......................... 435/243 |
| 6,444,467 | B1 | | 9/2002 | Fan et al. ................... 435/430.1 |
| 6,689,609 | B1 | | 2/2004 | Fan et al. ..................... 435/422 |
| 6,709,862 | B2 | | 3/2004 | Curtis .......................... 435/325 |
| 2002/0194649 | A1 | | 12/2002 | Fan et al. ..................... 800/298 |
| 2003/0061639 | A1 | | 3/2003 | Polonenko et al. .......... 800/298 |
| 2005/0124065 | A1 | | 6/2005 | Fan et al. ..................... 435/422 |

FOREIGN PATENT DOCUMENTS

| | | |
|---|---|---|
| CA | 2150489 | 12/2000 |
| EP | 1096849 B1 | 5/2001 |
| WO | WO 99/65291 A2 | 12/1999 |
| WO | WO 99/65293 A1 | 12/1999 |
| WO | WO 00/62599 A1 | 10/2000 |

OTHER PUBLICATIONS

Alvard et al. "Comparison of methods of liquid medium culture for banana micropropagation—Effects of temporary immersion of explants," Plant Cell. Tissue and Organ Culture; 32: 55-60, 1993.*

Ziv, M.; "Bioreactor Technology for Plant Micropropagation," Horticultural Reviews, vol. 24.; 2000; pp. 1-29.*

Hansen et al. "Recent advances in the transformation of plants," Trends in Plant Science Reviews, Jun. 1999, vol. 4, No. 6, pp. 226-231.*

Tautorus et al. "Somatic embryogenesis in conifers," Can. J. Bot. vol. 69, 1991, pp. 1873-1893.*

Ingram et al.; "Effect of bioreactor configuration on the growth and maturation of *Picea sitchensis* somatic embryo cultures," Plant Cell, Tissue and Organ Culture, 61: 87-90, 2000.*

Jackson, M.B.; ("Aeration Stress in Plant Tissue Cultures," Bulg. J. Plant Physiol., Special Issue, 2003, 96-109).*

Ziv, M.; "Bioreactor Technology for Plant Micropropagation," Horticultural Reviews, vol. 24; 2000; pp. 1-29.*

Ziv, M.; "Bioreactor Technology for Plant Micropropagation," Horticultural Reviews, vol. 24, 2000, pp. 1-24.*

Carlson and Hartle, 1995, "Manufactured Seeds of Woody Plants", S. Jain, P. Gupta & R. Newton (eds.), Somatic Embryogenesis in Woody Plants, vol. 1, 253-263.

Gray, et al., 1995, "Somatic Embryogenesis and the Technology of Synthetic Seed", Biotechnology in Agriculture and Forestry, vol. 30, 126-151.

Gupta and Grob, 1995, "Somatic Embryogenesis in Conifers", S. Jain, P. Gupta & R. Newton (eds.), Somatic Embryogenesis in Woody Plants, vol. 1, 81-98.

Kleinschmit, et al., 1993, "Past, Present, and Anticipated Applications of Clonal Forestry", Clonal Forestry II, Conservation and Application, Ed. By M.R. Ahuja and W.J. Libby, 8-41.

Park, et al., 1998, "Clonal Forestry", Forest Genetics and Tree Breeding, 143-167.

Redenbaugh, et al., 1993, "Synseeds—Applications of Synthetic Seeds to Crop Improvement", CRC Press, Inc., 35-46.

Roberts, et al., 1995, "A delivery system for naked somatic embryos of interior spruce", Automation and Environmental Control in Plant Tissue Culture, 245-256.

Sakamoto, et al., 1995, "Delivery systems for tissue culture by encapsulation", Automation and Environmental Control in Plant Tissue Culture, 215-243.

Sutton and Polonenko, 1999, "Commercialization of Plant Somatic Embryogenesis", Somatic Embryogenesis in Woody Plants, vol. 4, 263-291.

Tautorus, et al., 1991, "Somatic embryogenesis in conifers", Can. J. Bot. vol. 69, 1873-1899.

Attree, S.M. and Fowke, L.C., 1993, "Embryogeny of gymnosperms: advances in synthetic seed technology of conifers", Plant Cell, Tissue and Organ Culture, vol. 35, 1-35.

* cited by examiner

AERATED LIQUID PRIMING OF CONIFER SOMATIC GERMINANTS

CROSS-REFERENCE TO RELATED APPLICATIONS

This application claims the priority right of our prior co-pending provisional U.S. patent application Ser. No. 60/659,900 filed Mar. 10, 2005.

BACKGROUND OF THE INVENTION

1. Field of the Invention

This invention relates to the imbibition, germination and liquid priming of conifer somatic embryos. More particularly, the invention relates to the imbibition, germination and liquid priming of conifer somatic embryos in a manner that provides a scaleable and reproducible means of germinating and facilitating rapid early growth of conifer somatic embryos.

2. Background Art

The development and advancement of somatic embryogenesis as a vegetative propagation technology has made it possible to mass-produce genetically identical individual plants through the asexual reproduction of a source explant (Tautorus at al. 1991, Roberts et al. 1995). This technology can be applied in clonal forestry in plantation programs. The primary advantages of clonal forestry, as defined by Kleinschmit et al. (1993) and Park et al. (1998a), are: 1) the ability to capture a greater portion of the non-additive genetic gain from selected individuals within a breeding population; 2) the capability to rapidly introduce individuals with desirable traits to meet known site conditions; and 3) the ability to carefully plan genetic diversity into plantation programs.

Somatic embryogenesis of woody plants is generally a multi-step process (U.S. Pat. Nos. 4,957,866; 5,183,757; 5,294,549; 5,413,930; 5,464,769; 5,482,857, 5,506,136; the disclosure of all of which are herein incorporated by reference). No matter how diverse the different somatic embryogenesis protocols might be, the one common step is that somatic embryos must be germinated to produce somatic seedlings.

There are two standard approaches for germinating somatic embryos. The first employs conventional in vitro methods and the second uses encapsulation of somatic embryos to produce synthetic seed.

Conventional in vitro methods are generally based on the following steps. Initially, a naked somatic embryo (i.e., an embryo unprotected by any coatings) is sown, using aseptic techniques, onto a sterile semi-solid or liquid medium contained within a solid-support such as a Petri dish or a Phytatray® under sterile conditions, Next, after the somatic embryo has germinated under sterile conditions, the germinant is transplanted into conventional nursery growing systems. Generally, most protocols require that the germinants be autotrophic before they can be sown ex vitro. There are many disadvantages associated with in vitro protocols. The most significant are: 1) the repeated manual handling of each individual embryo in the germination and transplanting steps; 2) the stringent requirement for sterile techniques and culture conditions through all steps until somatic germinants are transplanted out of the in vitro germination environment into horticultural growing media; 3) the length of time (usually several weeks) of in vitro culture required to produce a germinant that is sufficiently robust to survive ex vitro; and 4) the difficulty in acclimatizing in vitro plantlets into ex vitro nursery environments. Therefore, the art of traditional in vitro protocols has an inherent nature of low efficiency and high cost. These characteristics are prohibitive to mass production of somatic seedlings. These undesirable characteristics make the commercial production of somatic seedlings less competitive than that of zygotic seedlings. Automation, including robotics and machine vision, may reduce or eliminate the extensive hand-handling that is currently necessary to germinate naked somatic embryos. However, no commercial equipment currently exists which can reliably, aseptically, and cost-effectively perform the in vitro protocols for germination of naked somatic embryos and subsequent transplanting into conventional propagation systems (Roberts et al., 1995; reviews by Sakamoto et al. 1995).

The second approach utilises encapsulation (generally gel-encapsulation) of the somatic embryos (Carlson and Hartle 1995, Gray et al., 1995; U.S. Pat. Nos. 4,562,663; 4,777,762; 4,957,866; 5,010,685; 5,183,757; 5,236,469; 5,427,593; 5,451,241; 6,486,218; 5,482,857 all of which are herein incorporated by reference) prior to germination. The embryos are encapsulated in various coating materials to form so-called "artificial seed", "synthetic seed" or "manufactured seed". This encapsulation process may or may not incorporate nutrients into the encapsulating medium, and provides a means by which the embryos can presumably be sown with conventional nursery seeding equipment (i.e., drum seeders or fluid drill seeders) into conventional nursery growing systems. The prior art makes references to sowing artificial seeds ex vitro into germination media comprised of soil or soil-less mixes, but in fact, the prior art only teaches methods for germinating artificial seeds in vitro, i.e., on sterilised semi-solid laboratory media. It appears that no practical approaches are taught or otherwise disclosed in the prior art for sowing encapsulated somatic embryos and/or artificial seed and/or manufactured seed into conventional growing systems using conventional sowing equipment.

There are also numerous biological and operational disadvantages inherent in using gel-encapsulated somatic embryos. Biologically, the most significant disadvantage is the much lower germination vigour and conversion success into plants than corresponding zygotic seeds, as seen in the prior art protocols for encapsulating or otherwise coating somatic embryos (Redenbaugh et al., 1993; Carlson & Hartle, 1995; Gray et al., 1995). This is in sharp contrast with the germination vigour and conversion success of non-encapsulated or non-coated somatic embryos, produced with methods disclosed in the art, and then sown using aseptic techniques onto in vitro germination media in sterile conditions. The in vitro sown somatic embryos can approximate those of the corresponding zygotic seeds (e.g., greater than 85%) (Gupta and Grob, 1995).

Timmis et al. (U.S. Pat. No. 5,119,588, incorporated herein by reference) recognised that "somatic embryos are too under-developed to survive in a natural soil environment" and therefore must be "cultured with an energy source, such as sucrose". They identify a method by which plant somatic embryos can be sown into horticultural containers filled with particulate soil-like substrates. Solutions containing compounds serving as carbon and energy sources and other nutrients, such as minerals and vitamins, are added to the substrates before or after the embryos are sown. Because such a "culture medium is highly susceptible to invasion by phytopathogens, which can result in death or retard the growth of the embryos", they teach that the containers, substrate, nutrient solutions and other components of their system must be biologically sterile. Somatic embryos must be sown into containers using aseptic techniques.

In the past, each sown container had to be kept biologically separated from the others and from the external environment and had to be kept in a sterile condition until the embryo had successfully germinated and developed into a complete, independent autotrophic plant. Only after autotrophy had been reached could the somatic seedlings be removed from the sterile conditions and then transplanted into a conventional commercial propagation environment. Even though the art taught by such methods may be practised to produce somatic seedlings, such methods are labour-intensive and bear characteristics of low efficiency, high cost and impracticability for mass production of somatic seedlings in a nursery environment.

There is a constant need for improvement of these techniques and methods in order to overcome the disadvantages of the germination and growth phases associated with somatic plant embryos. Improvements of high importance are those that would allow for shorter in vitro culture periods, reduced handling, opportunities for automation and the production of germinants or seedlings with high vigour.

SUMMARY OF THE INVENTION

An object of the present invention, at least in one form, is to provide a means of germinating and facilitating rapid early growth of conifer somatic embryos such that germinants can be sown ex vitro to convert into independent autotrophic plants at a good rate of success.

Another object of the present invention, at least in one form, is to provide a means to facilitate the separation of germinants with the highest growth potential from subtending tissues as well as from germinants less likely to exhibit vigorous growth ex vitro. This is intended to expedite sowing of germinants, increase the potential for seedling synchrony thus also reducing the need for excessive consolidation.

According to one exemplary aspect of the present invention, there is provided a process of priming mature, imbibed, germinated somatic embryos of a conifer species, which comprises: fully immersing mature, imbibed, germinated somatic conifer embryos in a sterile liquid nutrient medium, bubbling an oxygen-containing gas through the liquid nutrient medium containing the germinants to form an aerated embryo-containing nutrient medium, optionally exposing the aerated germinant-containing nutrient medium to light, at least intermittently, continuing the immersion, bubbling and optional exposure to light for a period of time effective to produce at least some successfully primed conifer germinants that are adapted for subsequent planting and conversion to viable seedlings, and removing the successfully primed conifer germinants from the nutrient medium.

Accordingly, in this aspect of the invention, enhanced environmental conditions are used during sterile (in vitro) culture to yield higher rates of germinant conversion when the germinants are planted in non-sterile (ex vitro) conditions.

The invention also relates to primed germinants and seedlings of conifer species produced by the above processes.

According to another exemplary aspect of the present invention, there is provided a process of producing seedlings of a conifer species from mature, imbibed, germinated and primed somatic conifer embryos, which comprises sowing mature, imbibed, germinated and primed somatic conifer embryos on a solid growing mix and exposing said embryos to light at an intensity in the range of 100-300 $\mu mol\, m^{-2}\, s^{-1}$ PPF under an atmosphere having a relative humidity of 75-85% and subjecting the embryos to applications of aqueous nutrient solution and water, wherein said mature, imbibed, germinated and primed somatic conifer embryos are previously embryos primed by the process defined above.

It is to be noted that the nutrient solution and solid growing mix indicated above preferably do not contain a sugar such as sucrose. However, the embryos are preferably contacted with a semi-solid medium containing organic nutrients and a carbohydrate, such as a sugar (e.g. sucrose), when sown on the solid growing mix. For example, the embryos may be partially inserted into a mass of the semi-solid medium which is itself supported by the solid growing mix.

According to yet another exemplary aspect of the invention, there is provided a method of selecting primed somatic germinants of a conifer species for subsequent planting and conversion to seedlings, which comprises suspending primed somatic germinants of a conifer species in an aqueous liquid medium, wherein said germinants include successfully primed conifer germinants that are adapted for subsequent planting and conversion to viable seedlings and unsuccessfully primed germinants, agitating the germinants in the medium, allowing the medium to stand without agitation, thereby allowing some of said germinants to settle to a bottom layer of said medium and others to float at a top layer of said medium, separating said germinants from said germinants settled at said bottom layer, and selecting said germinants from said top layer for subsequent planting and conversion to seedlings.

The above aspect of the invention is based on the finding that good (plantable) germinants often float and poor (unsuitable) germinants sink along with subtending tissue when agitated within an aqueous medium and allowed to stand.

This invention, at least in its preferred forms, provides a scaleable and reproducible means of germinating and facilitating rapid early growth of conifer (e.g. Loblolly pine) somatic embryos. This invention can (at least in its preferred forms) overcome bottlenecks in large-scale seedling production by providing one or more of the following advantages:

shortening the amount of time somatic embryos and germinants need to be maintained in sterile culture enabling scalability by providing methods for bulk germination as well as by incorporating the use of liquid culture for early germinant growth producing germinants of straight growth form (as compared to more curved growth form obtained with germination procedures employing semi-solid medium alone) that may enable more rapid sowing of germinants and better facilitate the development of automated means of sowing germinants eliminating the need for sterile conditions during early germinant growth prior to the establishment of autotrophy eliminating the need for high humidity and low light growth chambers to facilitate early ex vitro growth (conventional greenhouse environments are adequate for growth)

allowing for rapid conversion of germinants ex vitro allowing for high rates of conversion.

DEFINITIONS

Figure 1:
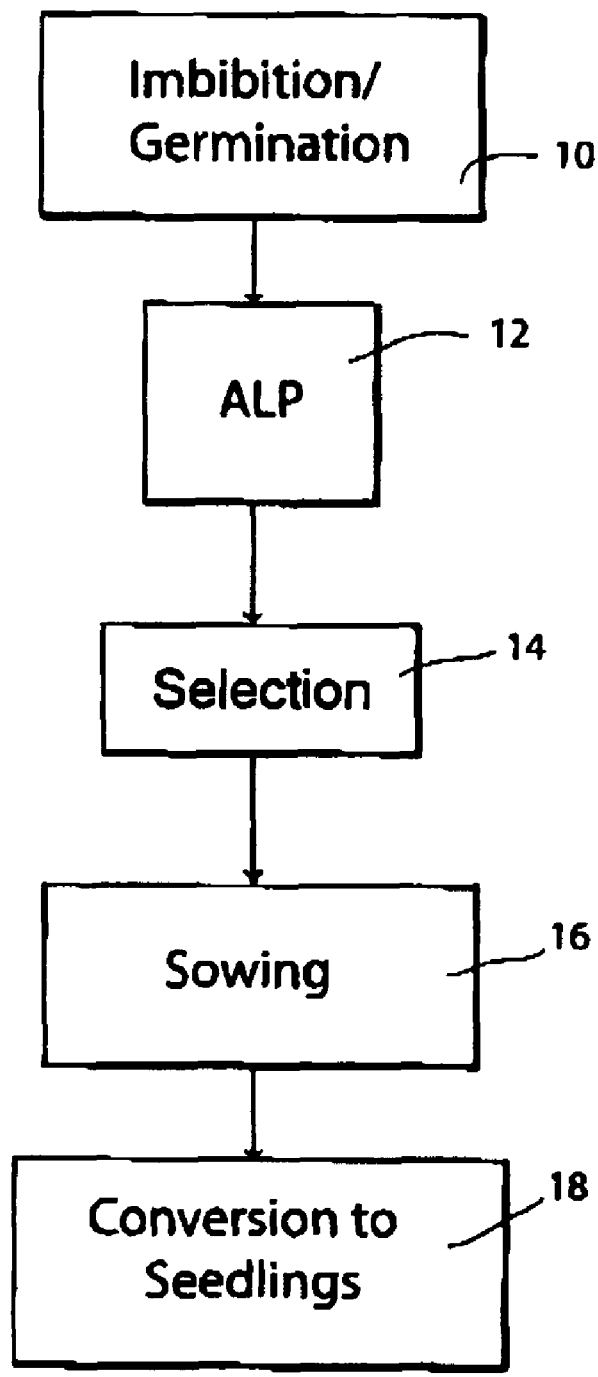
FIG. 1 is a schematic drawing illustrating steps in a method according to one form of the present invention.

A number of terms are known to vary in meaning in the literature describing this art. The following definitions are believed to be those most commonly used in the fields of botany and plant somatic embryogenesis, and are consistent with the usage of the terms in the present specification, including the claims. These definitions will assist in the understanding of the detailed description of the present invention that will follow.

"Autotrophic" refers to the stage of plant development in which the photosynthetic organelles, related enzymes and biochemical pathways are completely functional and capable of converting light energy, atmospheric carbon dioxide and water into the prerequisite carbohydrates (e.g., glucose) necessary to sustain further plant growth and development. Autotrophic plants are able to survive and grow under normal soil conditions.

"Conversion" refers to the transition from a heterotrophic stage of plant development to an autotrophic stage of plant development. The term "converted" as applied to a germinant means a germinant that has undergone conversion and is autotrophic.

"Desiccation" refers to the drying of a somatic embryo by any means to a water content less than that of the original hydrated embryo. Desiccation processes may include (a) mild desiccation, which encompasses water contents in the 36-55% water content range, and (b) severe desiccation, which occurs at water contents less than 36%, usually in the range of 5-30%. A fully desiccated viable embryo is able to survive freezing, and after rehydration, is able to successfully complete the germination process and convert to a normal, autotrophic plant.

"Frozen storage" refers to storage of embryos at less than the freezing point of water, and preferably at a temperature in the range of −10° C. to −196° C. (using liquid nitrogen), or more usually −10° C. to −80° C.

"Genotype" refers to the genetic constitution of an organism, acquired from its parents and available for transmission to its offspring. When used in the context of asexual plant propagation, genotype is interchangeable for clone.

"Germinant" refers to a somatic embryo that has been germinated but has not undergone conversion.

"Germination" refers to the process of contacting a mature somatic embryo with medium for any period of time until onset of autotrophic development.

"Heterotrophic" refers to the stage of plant development when the photosynthetic organelles, related enzymes and biochemical pathways are still not completely functional or capable of converting light energy, atmospheric carbon dioxide and water into the prerequisite carbohydrates (e.g., glucose) necessary to sustain further plant growth and development. Consequently, heterotrophic plants still require an exogenous supply of carbon and energy resources in the growth medium such as sucrose, to sustain normal growth and development until the plants become completely autotrophic. By definition, heterotrophic plants are not able to survive and grow under normal soil conditions.

"Imbibition" refers to the re-hydration of a desiccated somatic embryo such that its water content approaches that of the embryo when it was originally hydrated. An imbibed embryo is able to successfully complete the germination process and convert to a normal, autotrophic plant.

"Nutrients" are the inorganic micro- and macro-minerals, vitamins, hormones, organic supplements, and carbohydrates necessary for culture growth and somatic embryo germination.

"Nutrient solution" refers to water containing a dissolved nutrient or mixture of nutrients.

"Priming" refers to a treatment of plant embryos or germinants to promote vigorous growth.

"Root radicle" refers to the meristematic end of a germinating embryo from which roots develop. This is an area in which undifferentiated cell division is rapid, with the resulting cells then undergoing a period of elongation behind the root radicle before transformation into differentiated cells.

"Somatic embryo" refers to a plant embryo formed in vitro from vegetative (somatic) cells by mitotic division of cells. Early stage somatic embryos are morphologically similar to immature zygotic embryos, and comprise a region of embryonic cells subtended by elongated suspensor cells.

"Somatic embryogenesis" the process of initiation and development of embryos in vitro from somatic cells and tissues.

DETAILED DESCRIPTION OF THE INVENTION

The present invention, at least in one of its forms, is concerned with the imbibition, germination, priming and subsequent sowing of somatic embryos of conifer species. Priming involves exposing somatic embryos or germinants to a solution of nutrients, and optionally to light, following imbibition of desiccated embryos and germination of imbibed embryos to form germinants. Conventional methods of imbibition and germination may be employed to prepare germinants from mature desiccated embryos. In this regard, reference is made to U.S. Pat. No. 6,200,809, the disclosure of which is incorporated herein by reference. Imbibition and germination usually requires 1 to 14 days and in light and temperature conditions similar to those described below for the priming step.

The germinants are then subjected to a priming step referred to as aerated liquid priming (ALP). The reason for priming the germinants is to improve their rate of conversion into seedlings when sown in non-sterile conditions, e.g. in a greenhouse. Priming makes the germinants more robust and better able to withstand a harsh environment and exposure to disease-causing agents.

Aerated liquid priming is carried out by immersing germinants in an aqueous solution of nutrients while bubbling oxygen or an oxygen-containing gas (e.g. air or an oxygen-enriched gas) through the solution in order to keep the germinants in suspension or motion within the liquid. The use of oxygen or an oxygen-containing gas (e.g. air) for this purpose also exposes the germinants to oxygen which may be absorbed by the germinants and used for internal processes. Increasing levels of carbon dioxide would also be beneficial. While suspended in the liquid, the germinants are also preferably exposed to light, e.g. artificial light from a light source, to promote further development. The entire priming step is preferably carried out in sterile conditions to isolate the germinants at this stage from disease causing agents.

By keeping the germinants in suspension and motion (gentle agitation) during priming, rather than letting the germinants form an agglomeration or floating layer, the germinants can be kept out of prolonged contact with each other and thus have more surface area exposed for contact with the nutrient solution and oxygen. The submersion and gentle agitation by gas bubbles means that the germinants are subject to less stress during priming, and their constant motion means that they change orientation relative to the force of gravity and the direction of light, and thus have less tendency to adopt a bent or non-linear shape as the priming progresses. Germinants that are generally straight are found to have a better rate of conversion to seedlings than bent or distorted germinants. The agitation should be sufficient to achieve these advantages, but not so violent that embryo damage is caused.

Solutions employed for the aerated liquid priming step are aqueous solutions containing at least one source of carbohydrate. Although the preferred carbohydrate is sucrose, preferably present in the range of 1-6% (w/v), this invention can be practiced with sugars such as fructose, glucose, maltose, galactose, mannose, lactose and the like. Furthermore, the priming solution may contain, if so desired, a mixture of two or more carbohydrates. If carbohydrates other than sucrose, or if mixtures of carbohydrates, are used in the priming solution, then the appropriate concentrations of each carbohydrate should be determined in advance by the use of rate-selection studies. The design and performance of such rate-selection studies are known to persons skilled in the art.

In addition, the priming solution may also contain, if so desired, other types of nutrients which may further facilitate the various biochemical and physiological processes occurring during germination and growth. Such nutrients include, but are not limited to, inorganic minerals, vitamins and hormones. A non-limiting example of how this can be practiced is by adding to a solution containing sucrose in the range of 1-6% (w/v), a mixture of mineral nutrients formulated to deliver approximately 454 mg/l nitrogen, 81 mg/l phosphorus, 704 mg/l potassium, 50 mg/l calcium, 39 mg/l magnesium, 193 mg/l sulfur, 3 mg/l manganese, 0.5 mg/l zinc, 89 mg/l chlorine, 3 mg/l iron, 0.7 mg/l iodine, 0.6 mg/l boron, 0.01 mg/l molybdenum, 0.01 mg/l cobalt, and 0.01 mg/l copper. Furthermore, if so desired, IBA, a plant growth regulator, may be added alone at a concentration of 0.1 µM/l or in combination with one or both of GA and BA, each at a concentration of 0.1 µM/l. Also, ascorbic acid (vitamin C) may be added if so desired, at a concentration in the range of 10-1000 µM/l.

Furthermore, if so desired, pest control products such as antibiotics or fungicides may be added to the priming solution. A non-limiting example is the addition of benlate (0.1 g/l) end/or ampicillin (0.1 g/l). It is preferable during this step that the priming solutions be sterilized prior to the addition of the somatic germinants, and that an aseptic technique be used when adding embryos to the priming solution.

The imbibed germinants are generally primed in the priming solution under agitation by gas bubbling for a period of time preferably ranging from 6 hours to 10 days, preferably 24 hours to 6 days. It is a particular advantage of this invention, at least in its preferred forms, that such short periods of time can be employed for the priming step. This allows the period of time requiring sterile culture to be minimized and reduces the overall time for conversion to days rather than weeks, for conventionally germinated seedlings.

While it is possible to practice the priming step in absence of light, it is highly preferable to carry out the priming step in the presence of light for as much as 16 hours of light per day photoperiod at light intensities for example in the range of 5-50 but more preferably 20-50 µmolm-2 s-1 PPF (photosynthetically active radiation).

Mild temperatures may be used for the priming step, e.g. temperatures at ambient room levels or slightly higher (e.g. 27-30° C.).

The gas bubbling can be carried out in any suitable way, e.g. by providing a suitable priming vessel with a single or multiple holes in the bottom that are supplied with the gas under pressure, or even by dipping a hollow tube beneath the surface of the liquid and supplying a gas under pressure. Alternatively, gas spargers may be used to create fine bubbles. Most preferably, the amount of gas and position of the gas stream(s) should be such that the germinants are kept in constant motion (gentle agitation) without settling or layering and such that a recirculating current is set up in the priming vessel that maintains constant motion without requiring vigorous bubbling action that could damage the embryos. For this purpose, a single gas inlet may be provided in the bottom of the priming vessel, somewhat off-center in order to create a recirculation of liquid.

The priming vessel must of course have an outlet for the gas after the gas passes through the priming solution. The outlet may be constructed to prevent ingress of microorganisms or contaminants, e.g. it may have filtered port or a valve that seals the vessel tightly when the pressure in the vessel drops below a predetermined level.

After the period of priming, it is normal to observe germinants that appear healthy and germinants that do not. This is most evident when aeration is terminated and the solution allowed to stand without agitation. Most healthy plantable germinants float to the top of the liquid medium and most non-plantable germinants, as well as subtending tissue, will sink to the bottom of the vessel in most cases. The addition of water (or other solutions) can promote this effect. The plantable germinants can then be skimmed or filtered from the top of the solution in a rapid and efficient manner.

The priming procedure described above gives vigorous germinants that thrive well and can be planted ex vitro in non-sterile environments. The germinants can be sown naked directly into soil or a planting medium within a greenhouse setting instead of a horticultural chamber (such chambers have lower light levels and higher humidity, thus allowing pests to proliferate rapidly and reducing germinant survival rates). The conversion to seedlings can be carried out in a manner similar to that used for zygotic seedlings, although careful watering may be required to prevent drying out of the germinants until they become autotrophic. Watering by soaking, misting or spraying may be employed. Preferred temperatures are within the range of 15-35° C., relative humidities may be in the range of 75-100%, and light intensities may be 10-500 foot candles, and diurnal cycles of 6 hours day/18 hours night to 22 hours day/2 hours night may be employed. After the seedlings become autotrophic, they can be treated in the same manner as commercial seedlings from any source.

Conversion rates are significantly increased if a semi-solid medium is applied on top of the conventional growing medium in contact with the germinants. Such a medium is disclosed in our co-pending U.S. application Ser. No. 10/726,574 filed Dec. 3, 2003, published on Jun. 9, 2005 as US patent publication no. 2005-0124065 A1, the disclosure of which is incorporated herein by reference. This improves root/soil contact, preventing desiccation, and can provide nutrients to the germinants to assist growth until autotrophy is established.

The priming step is effective for Loblolly pine (*Pinus taeda*) and other conifer species, e.g. Eastern white pine (*pinus strobus*), White spruce (*Picea glauca*), Black spruce (*Picea maniana*), Jack pine (*Pinus banksiana*), Red Pine (*Pinus resinosa*), Northern white cedar (*Thuia occidentalis*), Eastern hemlock (*Tsuga Canadensis*), etc.

In summary, FIG. 1 of the accompanying drawings shows the steps described above. Germinants are prepared by imbibition and germination 10 and are then subjected to priming under gas bubbling 12 (referred to loosely as "aerated liquid priming" or ALP). Germinant selection 14 is then normally required to select the plantable germinants (carried out either by hand or automatically, with or without flotation), followed by sowing 16 and conversion to seedlings 18, e.g. in a greenhouse setting.

Figure 2:
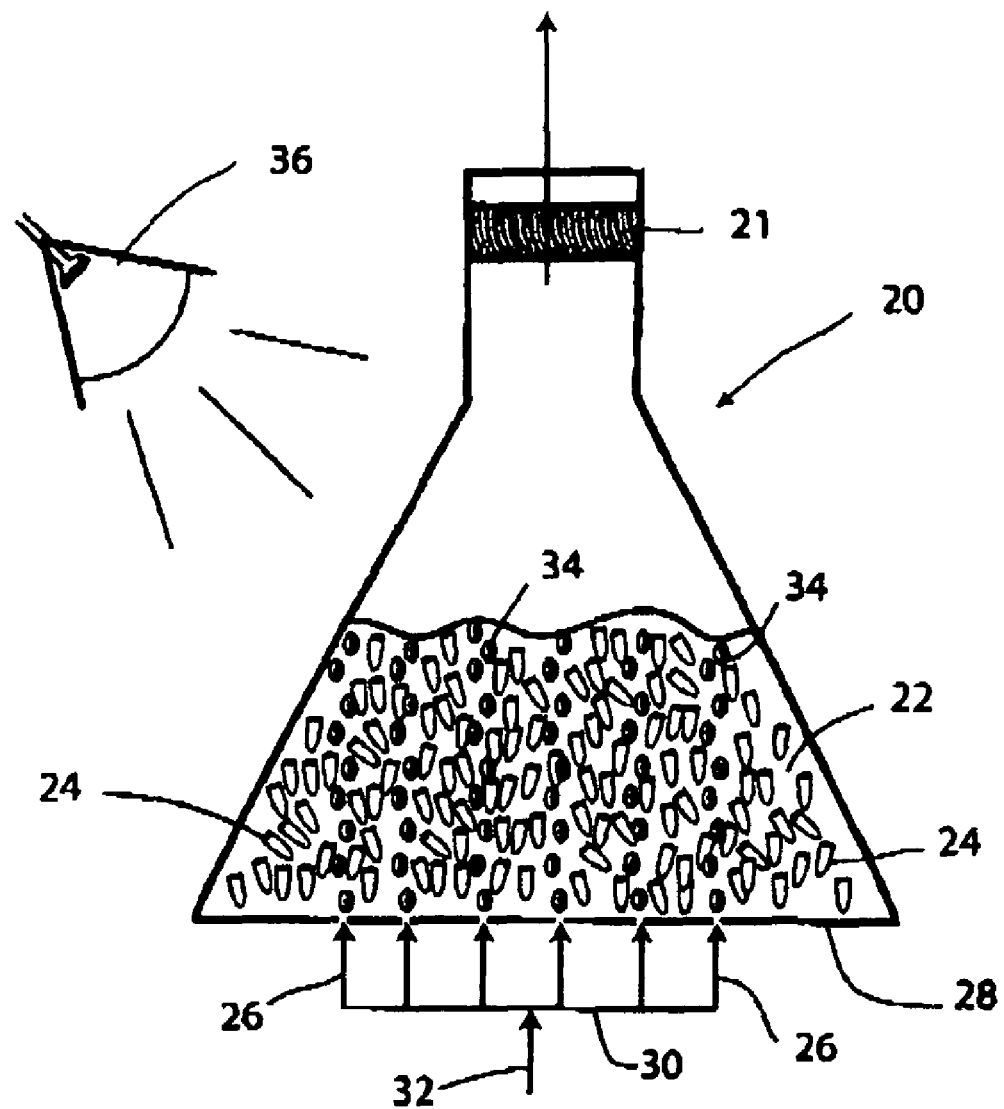
FIG. 2 is a simplified illustration of a priming vessel, priming medium and germinants suitable for use in the present invention.

FIG. 2 is a simplified representation of a priming vessel 20 containing a priming medium 22 and submerged germinants 24. A gas is introduced into the vessel from the bottom via tubes 26 that pass through the bottom wall 28 of the vessel. The gas exits at the upper end of the vessel (as shown by the arrow) after passing through a filter 21. The tubes 26 are connected to a manifold 30 that is supplied with gas under pressure via a single input tube 32. The gas introduced in this way forms streams of bubbles 34 that agitate the germinants during the priming step. A light source 36 is provided to irradiate the germinants as they are primed. At the end of the priming step, the gas supply is turned off and the germinants allowed to separate into those that float (plantable) and those that sink (not plantable). The plantable primed germinants can then be skimmed or filtered off.

The following is a preferred protocol for carrying out the invention. Mature, fresh or desiccated (<10 wt % moisture content) conifer somatic embryos are placed, with filter paper, on semi-solid germination medium for 7 days to achieve imbibition and subsequent early germination. Chamber conditions during imbibition and germination include 16 hr light per day photoperiod (periods of 12-24 hrs were tested) at 20-50 $\mu molm^{-2} s^{-1}$ PPF with chamber temperature at 27-30° C. At the end of the culture period on semi-solid medium, germinants are primed for 5 days in an aerated liquid priming (ALP) system, which involved constant immersion of germinants in aerated rm8GMD liquid medium (Table 1 below).

TABLE 1

Macro nutrients, micronutrients and vitamins in rm8GMD

| Basal salts (* heat sensitive) | Amount (mg) per liter Medium |
|---|---|
| Major | |
| Ca(NO$_3$)$_2$·4H$_2$O | 236.2 |
| MgSO$_4$—7H$_2$O | 493 |
| K$_2$SO$_4$ | 173.7 |
| KNO$_3$ | 556.05 |
| NH$_4$H$_2$PO$_4$ | 862.5 |
| KH$_2$PO$_4$ | 204.1 |
| Minor | |
| KI | 0.88 |
| H$_3$BO$_3$ | 3.09 |
| MnSO$_4$—H$_2$O | 11.18 |
| ZnSO$_4$—7H$_2$0 | 2.04 |
| CuSO$_4$—5H$_2$0 | 0.5 |
| Na$_2$MoO$_4$—2H$_2$0 | 0.024 |
| CoCl$_2$—6H$_2$0 | 0.024 |
| Iron | |
| 7% Fe chelate (chelated with DTPA) | 80 |
| Vitamins | |
| myo-Inositol | 50 |
| Thiamine HCl(B$_1$) | 5 |
| Pyridoxine HCl (B$_6$) | 1 |
| Nicotinic Acid | 1.97 |
| *Pantothenic acid (B$_5$) | 0.2 |
| *Cyanocobalamin (B$_{12}$) | 0.1 |
| *L-Ascorbic acid (20–200 mesh) | 17.61 |

Chamber conditions during priming include 16 hr light per day photoperiod at 20-50 $\mu molm^{-2} s^{-1}$ PPF (a range of 5-200 PPF was tested and 20-200 gave the best conversion). Early results (9-10 weeks) showed 20-50 PPF was best. In later weeks treatments with high light levels caught up in conversion rates. The temperature is maintained at 27-30° C. The airflow rate during priming is 750-1500 ml/min (as measured at system exhaust) (note a range of 301-500 ml/min was tested—flow to ensure germinants do not remain settled is required). A 10 g FW of embryos and tissues is added per each priming vessel with 500 ml rm8 GMD priming medium in the ALP system (Note: Vessel sizes of 1, 2, 5 and 20 L were tested). After priming, germinants that met acceptable morphology (no deformities) are selected and sown ex vitro. Germinants are then sown into a germination medium comprising particles of a solid component held within a flowable component containing water and a carbohydrate nutrient for the germinant (as disclosed in our co-pending application Ser. No. 10/726,574). The germination medium is preferably provided in cavities in polymerized peat miniplugs in styrofoam trays. Germinants are sown such that roots or root radicles and part of the hypocotyl are covered by the medium. Trays with germinants are then maintained in a greenhouse environment (~85% RH, 100-300 $\mu molm^{-2} s^{-1}$ PPF) with standard watering and fertilization regimes. This protocol yields up to 50-60% conversion rates for Loblolly pine germinants.

In addition, at the end of priming, it is possible to separate the majority of germinants meeting planting criteria from tissues as well as germinants not meeting planting criteria by adding water or (or other solutions) to the ALP vessel. This results in the majority of germinants meeting planting criteria floating to the top of the vessel where they can be separated from other material in the vessel by decanting. This has the effect of greatly simplifying the process of selecting germinants meeting planting criteria.

The success of this protocol is influenced by the environmental conditions applied during germinant growth in vitro and ex vitro. For in vitro steps of this process, light conditions and aeration have significant impacts on ex vitro germinant survival and conversion. The result is the production of a germinant with a greater level of stress resistance. For ex vitro growth, the prior art has recommended extremely mild ex vitro growing conditions are preferably employed including low light (30-50 $\mu molm^{-2} s^{-1}$ PAR) and high humidity (>90% RH) for at least the initial part of the ex vitro culture period. During the development of this invention, it was found that such conditions can be detrimental to germinants and negatively impacts germinant survival and conversion. Instead, conditions that are easily attainable in greenhouse environments (100-300 $\mu molm^{-2} s^{-1}$ PPF light with ~85% RH) are preferred for this invention and such conditions can be used to promote rapid germinant growth and conversion. An additional benefit is that outbreaks of disease are dramatically reduced because germinants are able to develop in this lower humidity environment (i.e., greenhouse pest outbreaks increase dramatically at >90% RH).

EXAMPLES

Standard Methods and Conditions for Ex Vitro Culture

Below is a list of protocols that were applied when sowing germinants ex vitro after they had been prepared by aerated liquid priming (ALP) as presented in the detailed description of the invention. The examples describe loblolly pine, but radiata pine has also been tested and found to germinate and convert in the nursery at high frequency.

Germinant establishment medium (GEM) was prepared as described by Fan et al. in U.S. patent application Ser. No. 10/726,574.

Block Sanitizing and Fertilizing

Prior to sowing and GEM dispensing, miniblocks and rooting sponges were sanitized by applying hot water so that the rooting sponge reached a temperature of 65° C. Miniblocks were then leached with plain water to lower EC levels in blocks. The miniblocks were then fertilized with 'Starter mix' fertilizer (e.g., 11-41-8 NPK) at 50 ppm nitrogen.

Survival, Conversion and Merchantability Assessments

Survival was determined by counting the number of germinants that were green and appeared to be viable at the time of assessment. Conversion was determined by counting the number of surviving plants that had epicotyl and a well developed root system. Percent survival and conversion represented the percent of the total number of germinants sown that had survived or converted. A merchantable seedling was defined as a seedling that had a shoot height (including epicotyl) of between 2.5 and 5.0 cm and had a root system that was well developed throughout the rooting sponge. A seedling of these qualities would be able to be transplanted to larger containers or into a bare root nursery.

Greenhouse Conditions

Listed below are the greenhouse environmental conditions that the germinants were transitioned through during seedling growth.
1) Temperature: from 22 to 16° C.
2) Lighting: from 25 W m$^{-2}$ to 250 W m$^{-2}$
3) Humidity: from 85-92% RH to 50-70% relative humidity
4) Fertigation: from 11-41-8 NPK at 50 ppm N to 19-9-18 NPK at 100 ppm N
5) Pest control—0.1 g/l benlate, 0.1 g/l ampicillin or other anti-fungal, anti-bacterial or pesticide solutions were used to control fungi, bacteria and pests when needed.

Standard Methods and Conditions for In Vitro Culture

The protocol included a 1-week imbibition and germination of desiccated loblolly pine embryos on germination medium, and environmental conditions included 16 hrs light/day (at 20-50 μmolm-2 s-1 PPF) and 27-30° C. air temperature. Germinant preparation continued with a 5 day aerated liquid priming (ALP) in rm8GMD medium with environmental conditions including 16 hrs light/day (at 20-50 μmolm-2 s-1 PPF), aeration of 750-1500 ml/min, and an air temperature of 27-30° C. Note that airflow rate was measured at the exhaust filter of the ALP system. A maximum of 10 g FW (fresh weight) of embryos and tissues was added per each 500 ml liquid medium (rm8GMD) in priming flasks.

Ex vitro culture occurred in a greenhouse environment (i.e. not in a horticultural growth chamber) where conditions were as described under "Standard Methods and Conditions". Each of the miniplugs had 0.4 ml of GEM added to a small cavity in the top of the miniplug.

Example 1

Large scale production of seedlings from somatic embryos necessitates the use of a greenhouse as a suitable growing environment to promote the conversion of young germinants. In order to circumvent the need to use high humidity chambers (or other mild environments) for early growth after sowing and prior to transfer to a greenhouse environment, it is necessary that germinants grow vigorously and are readily able to adapt their environment. The methods described for producing germinants using the ALP system of the present invention results in germinants that meet these requirements. This trial showed that loblolly pine germinants selected for sowing ex vitro after ALP could be sown and transferred directly into a greenhouse environment rather than having early growth take place in a chamber.

Methods

During in vitro culture, this trial applied all of the same methods and conditions that are detailed in the "Standard Methods and Conditions for In Vitro Culture" section. In this trial, a number of different ex vitro environments were tested for their effect on germinant survival and conversion. The treatments used in this trial are listed in Table 2. The conditions in the low light chamber were as follows: light intensity 10-20 μmol m$^{-2}$ s$^{-1}$ PPF, 18 hour photoperiod, 22-26° C. air temperature, 95-100% RH, and 1000-1500 ppm $CO_2$. Conditions in the high light chamber were as follows: light intensity 100-150 μmol m$^{-2}$ s$^{-1}$ PPF, 18 hour photoperiod, 22-26° C. air temperature, 80-90% RH, and 1000-1500 ppm $CO_2$.

Two lines of desiccated loblolly pine somatic embryos were used in this example, lines E and A. For E, two replicates of 49 germinants were sown ex vitro for each treatment. For A, two replicates of 25 germinants were sown for each treatment except for treatment 1 (Table 2) in which one replicate had 49 germinants sown and one had 25 germinants sown.

TABLE 2

Treatments tested in Example 1

| Treatment | Weeks in low light, high humidity chamber | Weeks in high light, high humidity chamber | Weeks in chamber before transfer to greenhouse |
|---|---|---|---|
| 1 | 1 | 2 | 3 |
| 2 | 0 | 3 | 3 |
| 3 | 1 | 1 | 2 |
| 4 | 0 | 2 | 2 |
| 5 | 0 | 0 | 0 |

Results and Discussion

A two-way Analysis of Variance (line×treatment) for results obtained for survival at 10 weeks (Table 3) after sowing showed that there was a significant treatment effect on survival for lines E and A combined (p=0.001). There was no significant line×treatment interaction (p=0.112). A Tukey post-test for the two lines combined showed that all treatments in which germinants were maintained in a chamber for any period of time had significantly lower survival rates than the treatment in which germinants were placed in a greenhouse immediately after sowing (p≦0.012).

A two-way ANOVA for results obtained for conversion at 10 weeks showed that although the treatment effect was significant (p<0.001) there was a significant line×treatment interaction (p=0.023), so results were further analyzed for each line separately using a one-way ANOVA. Tukey post-tests were used for pair-wise comparisons between treatments for a given line. For E, treatments in which germinants were kept in chambers for 3 weeks prior to a transfer to a greenhouse had significantly lower conversion rates than germinants placed directly in a greenhouse after sowing (p≦0.018).

TABLE 3

Percent survival and conversion at 10 weeks after sowing

| Genotype | Treatment | Ex vitro Condition | % Survival | Std. Error | % Conversion | Std. Error |
|---|---|---|---|---|---|---|
| E | 1 | 1 wk low light chamber, 2 wks higher light chamber, move to GH wk 4 | 42 | 7 | 25.5 | 5.5 |
| E | 2 | 3 wks high light chamber, move to GH wk 4 | 30 | 3 | 22 | 2 |
| E | 3 | 1 wk low light chamber, 1 wk higher light chamber, move to GH wk 3 | 46 | 7 | 35 | 4 |
| E | 4 | 2 wks high light chamber, move to Greenhouse wk 3 | 50 | 11 | 35 | 6 |
| E | 5 | Greenhouse Only | 63 | 2 | 56 | 1 |
| A | 1 | 1 wk low light chamber, 2 wks higher light chamber, move to GH wk 4 | 23 | 13 | 21 | 11 |
| A | 2 | 3 wks high light chamber, move to GH wk 4 | 16 | 0 | 4 | 0 |
| A | 3 | 1 wk low light chamber, 1 wk higher light chamber, move to GH wk 3 | 34 | 6 | 24 | 0 |
| A | 4 | 2 wks high light chamber, move to Greenhouse wk 3 | 20 | 4 | 8 | 0 |
| A | 5 | Greenhouse only | 74 | 2 | 66 | 2 |

Germinants maintained only 2 weeks in chambers did not have significantly lower conversion rates than germinants placed in a greenhouse at sowing ($p \leq 0.077$). This suggests that this line may be tolerant to a range of ex vitro environments. However the mean conversion rates for the two treatments in which germinants were kept in chambers for 2 weeks was 13% to 17% lower than the conversion rate obtained for germinants placed directly in the greenhouse. Such lower conversion rates would likely increase the costs of any large scale seedling production scenario. Further, there would be no cost saving advantage to using growth chambers as compared to using greenhouses as growing environments.

For line A, ANOVA followed by a Tukey post-test showed all treatments in which germinants were maintained in a chamber for any length of time had a significantly lower conversion rate than germinants that were placed in the greenhouse immediately after sowing ($p \leq 0.010$). It is possible that the lower survival and conversion rates observed in the growth chambers were due in part to lower light conditions in the chambers as compared to in the greenhouse. In the sustained high humidity environment present in the growth chambers, fungi and bacteria are able to grow rapidly and this may also explain in part the poorer performance of germinants maintained in chambers.

Conclusions

Germinants produced using methods described for imbibition, germination and ALP have higher survival and conversion rates when placed directly in a greenhouse environment as compared to when germinants are placed in small growth chambers. The methods described result in germinants that would be amenable to large-scale production since using a greenhouse as a growing environment would significantly reduce costs for growing seedlings.

Example 2

The purpose of this example was to demonstrate the effects that duration of in vitro culture can have on loblolly pine germinant survival and conversion ex vitro. The duration of in vitro culture can have an impact on both germinant morphology and stress tolerance and can influence germinant success ex vitro.

This trial tested the effects of varying the length of time used for in vitro culture on the yield of germinants that could be selected for sowing ex vitro. Two aspects of in vitro culture were varied including the length of time that germinants were kept on semi-solid medium, and the duration of ALP. During in vitro culture, somatic embryos germinate and elongate. The period of in vitro culture should yield germinants that have grown such that the majority of germinants meet selection criteria based on morphology. In the best case scenario, the in vitro culture will allow as many germinants to grow to meet selection criteria as possible based on the number of viable somatic embryos that are put into the system.

Methods

In this trial germinants were placed on semi-solid medium for either 1, 3, or 7 days and then moved to ALP for either 3 or 5 days (Table 4). Conditions during imbibition and ALP were as they are described above (in Standard Methods and Conditions for In Vitro Culture), except the photoperiod in chambers was set for 12 hours of light/day. Two lines were tested in the treatments including A and D. This experiment served as a preliminary trial to determine what duration of in vitro culture was necessary to maximize the yield of germinants that could be selected for sowing.

A number of potentially viable somatic embryos (a maximum of 260 for A and 200 for D) were placed in each treatment group. Embryos and tissues originating from 4 Petri plates of maturation medium were each added to one ALP vessel. A separate vessel was used for each treatment. At the end of ALP, germinants that met the following criteria were selected as germinants that could potentially be sown: 1) at least 3 well developed cotyledons symmetrical around long axis, 2) green, 3) elongated at least 5 mm in total length, and 4) straight or no bends greater than 90 degrees.

TABLE 4

Treatments applied to vary the duration of in vitro culture

| Treatment | Days on semi-solid medium | Days in ALP | Total number of days for in vitro culture |
|---|---|---|---|
| 1 | 1 | 3 | 4 |
| 2 | 1 | 5 | 6 |
| 3 | 3 | 3 | 6 |
| 4 | 3 | 5 | 8 |
| 5 | 7 | 3 | 10 |
| 6 | 7 | 5 | 12 |

Results and Discussion

Figure 3A:
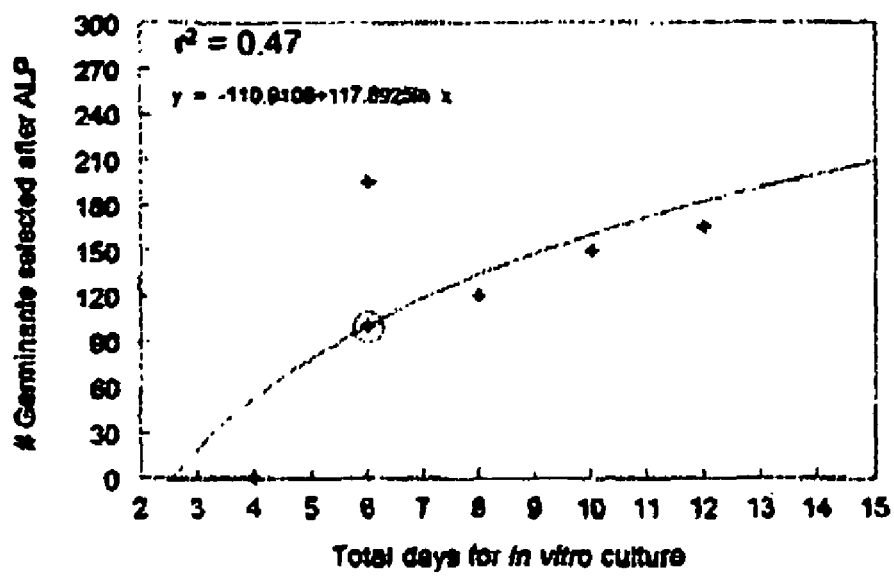
FIGS. 3A, 3B, 3C and 3D are graphs showing results of Examples described below.
Figure 3B:
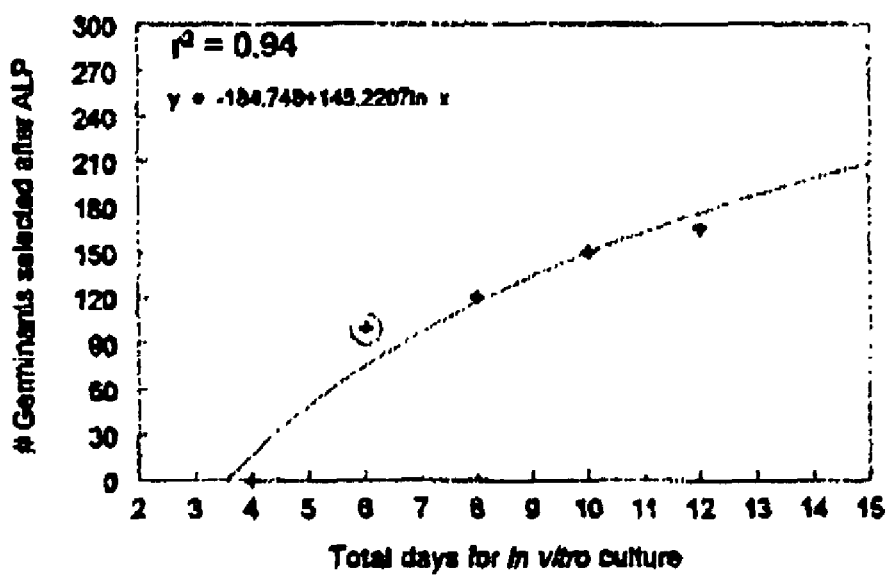
Figure 3C:
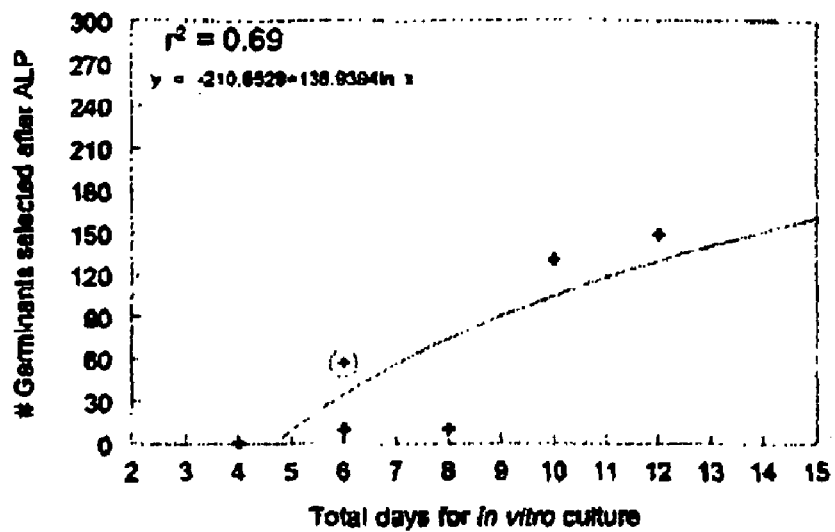

Results from this trial showed that, generally, as total time of in vitro culture increased towards 12 days, a higher the yield of germinants meeting the criteria for selection was obtained (FIG. 3A, 3B, 3C). However, as the total time of culture increased, the benefits of prolonged culture, in terms of increasing numbers of selectable germinants, reduced. For both lines A and D, the increase in the number of germinants selected between 10 and 12 days of in vitro culture was the lowest as compared to all other increases observed between treatments including a shorter and a longer culture period.

For line D, the highest number of germinants selected was obtained with the longest culture period (12 days including 7 days on semi-solid medium and 5 days in ALP). A good correlation between the curve fit and the data was observed with all data points included in the analysis ($r^2=0.69$). For line A, the highest number of germinants selected was observed for treatment 3; however, this result appeared to be an outlier when compared to results for other treatments, When this data point was removed before curve fitting the data, $r^2$ showed a more robust correlation between date and the curve fit ($r^2=0.47$ treatment 3 included in analysis, $r^2=0.94$ treatment 3 excluded). Given that the number of viable somatic embryos added to each treatment was approximate, it is possible that a higher number of viable embryos were inadvertently added to treatment 3 than to other treatments.

FIG. 3A of the accompanying drawings shows the number of germinants meeting selection criteria for line A. Treatments 2 and 3 both included 6 day total culture periods. The result for treatment 2 is circled.

FIG. 3B of the accompanying drawings shows germinants meeting selection criteria for line A. Treatment 3 is excluded. The result for treatment 2 is circled.

FIG. 3C of the accompanying drawings shows germinants meeting selection criteria for line D. Treatments 2 and 3 both included 6 day total culture periods. The result for treatment 2 is circled.

Conclusions

Varying conditions during in vitro culture can impact the yield of germinants that can be selected for sowing. This trial demonstrated that a range of durations of in vitro culture period can be applied to obtain germinants that could be selected for sowing; however, among the treatments tested, a culture period including 7 days on semi-solid medium and 5 days of ALP may produce the best yield of germinants.

Example 3

In this example, a range of ALP durations, following a consistent 7 day culture period on semi-solid medium, were compared to determine the effects of ALP duration on germinant yield as well as on germinant survival and conversion ex vitro.

Methods

Desiccated embryos from lines B and F were placed on semi-solid medium for imbibition and germination for 7 days. The density of embryos with tissues per each Petri plate of semi-solid medium was kept relatively consistent within each line tested. Chamber conditions during culture on semi-solid medium included 16 hr light per day at 20-50 µmolm-2 s-1 PPF, with air temperature at 27-30° C. At the end of imbibition, germinants were put in ALP for 2, 4, 5, 6, 8 or 10 days (Table 5). Conditions during ALP included 16 hr light per day at 20-50 µmolm-2 s-1 PPF, with air temperature at 27-30° C. Airflow rate was adjusted to 750-1500 ml/min as measured at the flask exhaust filter. A maximum of 10 g FW of embryos and tissues was added to 500 mls rm8GMD medium in each ALP vessel. The number of Petri plates with germinants put into ALP was recorded for each priming vessel.

TABLE 5

Treatments testing effects of duration of ALP

| Treatment | Semi-solid medium (days) | ALP (days) | Total Germinant Preparation Time (days) |
|---|---|---|---|
| 1 | 7 | 2 | 9 |
| 2 | 7 | 4 | 11 |
| 3 | 7 | 5 | 12 |
| 4 | 7 | 6 | 13 |
| 5 | 7 | 8 | 15 |
| 6 | 7 | 10 | 17 |

After ALP, germinants were evaluated. The number of germinants per ALP vessel that met selection criteria was recorded. In addition growth, measured as total length and root length for a random subsample of 30 germinants per treatment, was also assessed. Germinants meeting selection criteria were sown in miniplugs with GEM. Three replicates of germinants from each treatment were sown (Table 6). Replicates were not always equivalent across treatments since different durations of ALP resulted in different germinant yields. Germinants were maintained in a greenhouse during ex vitro growth. Criteria for selecting germinants for sowing were as follows: 1) at least 3 well developed cotyledons symmetrical around long axis, 2) green, 3) elongated to at least 5 mm in hypocotyl length, and 4) straight or no bends greater than 90 degrees.

TABLE 6

Number of germinants sown for each ALP treatment

| Genotype | ALP Duration (days) | Total # of planted germinants | Total # of replicates sown | Mean germinants sown per replicate |
|---|---|---|---|---|
| B | 2 | 84 | 3 | 28.0 |
| F | 2 | 42 | 3 | 14.0 |
| B | 4 | 68 | 3 | 22.7 |
| F | 4 | 28 | 3 | 9.3 |
| B | 5 | 186 | 3 | 62.0 |
| F | 5 | 96 | 3 | 32.0 |
| B | 6 | 198 | 3 | 66.0 |
| F | 6 | 106 | 3 | 35.3 |
| B | 8 | 249 | 3 | 83.0 |
| F | 8 | 111 | 3 | 37.0 |
| B | 10 | 257 | 3 | 85.7 |
| F | 10 | 176 | 3 | 58.7 |

Results and Discussion

Figure 3D:
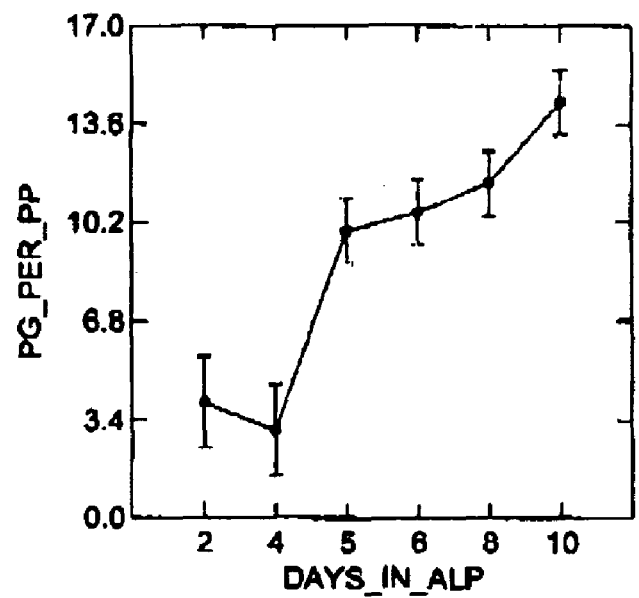

In general, increasing the duration of ALP increased the yield of germinants that met the criteria for selecting germinants to sow ex vitro (FIG. 3D). Two-way ANOVA (line×days in ALP treatment) showed that there was a significant line effect (p=0.001) and treatment effect (p=0.003) on germinant yield (PG/pp), but there was no significant interaction of these variables (p=0.554). A Tukey Pairwise Comparison showed that for the two lines combined, there were no significant differences in germinant yield among treatments with 5 or more days for ALP (p≧0.154). For both 2 and 4 day ALP treatments, germinant yield was significantly lower than some other treatments. With 2 day long ALP, germinant yield was significantly lower than yields obtained with 8 and 10 day ALP (p≦0.037). With 4 day ALP, yield was significantly lower than 6 to 10 day ALP (p≦0.038).

FIG. 3D of the accompanying drawings shows the Least Squares Means for combined germinant yield data for lines B and F. The yield was calculated as germinants selected for planting (PG) per each Petri plate (pp) of germinants placed in ALP after culture on semi-solid medium.

Measurements taken after ALP showed that germinant shoots continued to elongate during ALP (Table 7). This could explain in part why more germinants per Petri plate put into ALP vessels met selection criteria as the duration of ALP increased. Analysis of growth data showed that for B, there was no significant difference in total length for treatments with 2, 4, 5, and 6 days of ALP (p≧0.495). Treatments with 8 and 10 days of ALP were not significantly different from each other (p=0.999), but these germinants were significantly longer than germinants in all other treatments with shorter durations of ALP (p≦0.004). There were no differences in root lengths (p≧0.450) for this line. For F, there were no significant differences in germinant total length for treatments with 2, 4, 5, and 6 days of ALP (p≧0.317). Treatments where ALP was applied for 8 and 10 days were not significantly different from each other (p=0.056), but these treatments were significantly different from all other treatments (p<0.001). As in line B, there were no significant differences in root lengths (p≧0.541) for F.

TABLE 7

Mean germinant and root lengths (n = 30) following ALP

| ALP Duration (days) | Total length (mm) | Standard Error | Root length (mm) | Standard Error |
|---|---|---|---|---|
| B | | | | |
| 2 | 9.73 | 0.33 | 2.85 | 0.18 |
| 4 | 9.22 | 0.46 | 2.18 | 0.32 |
| 5 | 11.05 | 0.71 | 3.27 | 0.48 |
| 6 | 10.52 | 0.74 | 2.52 | 0.48 |
| 8 | 15.20 | 0.99 | 2.23 | 0.50 |
| 10 | 14.80 | 0.96 | 2.53 | 0.46 |
| F | | | | |
| 2 | 7.78 | 0.27 | 1.83 | 0.20 |
| 4 | 9.66 | 0.46 | 1.54 | 0.31 |
| 5 | 8.87 | 0.45 | 1.95 | 0.30 |
| 6 | 9.35 | 0.49 | 1.83 | 0.31 |
| 8 | 16.93 | 1.07 | 2.37 | 0.54 |
| 10 | 14.40 | 0.75 | 1.60 | 0.29 |

It was observed that for treatments with >6 days of ALP, germinants were somewhat soft, especially at the roots, as compared to germinants that were in ALP for shorter lengths of time. In addition, results from assessments made at 12 weeks after sowing germinants ex vitro showed that germinants kept in ALP for 8 and 10 days had lower survival and conversion rates than germinants kept in ALP for shorter periods of time (Table 8). One-way ANOVA slowed significant treatment effects for both lines tested in this trial (p<0.001).

TABLE 8

Mean percent survival and conversion at 12 weeks

| ALP Duration (days) | %-Survival | Standard Error | %-Conversion | Standard Error |
|---|---|---|---|---|
| Line B | | | | |
| 2 | 61.90 | 8.34 | 55.97 | 6.32 |
| 4 | 67.53 | 2.11 | 64.63 | 1.03 |
| 5 | 53.23 | 1.63 | 45.17 | 1.63 |
| 6 | 68.17 | 6.13 | 62.10 | 4.39 |
| 8 | 3.20 | 1.70 | 3.20 | 1.70 |
| 10 | 32.60 | 5.56 | 32.60 | 5.56 |
| Line F | | | | |
| 2 | 71.43 | 10.91 | 69.07 | 9.53 |
| 4 | 78.53 | 0.73 | 78.53 | 0.73 |
| 5 | 65.73 | 9.66 | 61.57 | 9.24 |
| 6 | 75.43 | 2.03 | 74.50 | 1.68 |
| 8 | 9.90 | 6.30 | 9.90 | 6.30 |
| 10 | 25.07 | 6.07 | 25.07 | 6.07 |

Tukey Pairwise Comparison showed that for line B, there were no significant differences among treatments with 2 to 6 days of ALP prior to sowing germinants ex vitro (p≧0.100). Treatments with 2 to 6 days of ALP all had significantly higher conversion rates than germinants maintained in ALP for 8 days (p<0.001). In addition, treatments with 2, 4 and 6 days of ALP had significantly higher (p≦0.035) conversion rates than the treatment with 10 days of ALP; although germinants with 5 days of ALP before sowing did not differ from this treatment. For line F, there were no significant differences in conversion rates among treatments with 2 to 6 days of ALP prior to sowing germinants ex vitro (p≧0.500). Treatments with 2 to 6 days of Alp all had significantly higher conversion rates than germinants maintained in ALP for 8 and 10 days (p<0.014). For B, germinants with 8 days of ALP had a significantly lower conversion rate than germinants kept in ALP for 10 days (p=0.006), for F these treatments did not produce significantly different results (p=0.617). For the best treatments tested (i.e. ALP 2 to 6 days in duration), conversion rates were ~57% for B and ~71% for F. This result surpasses the expected conversion rate of 50-60%.

FIG. 3D of the accompanying drawings shows the Least Squares Means for combined germinant yield data for lines B and F. The yield was calculated as germinants selected for planting (PG) per each Petri plate (pp) of germinants paced in ALP after culture on semi-solid medium.

CONCLUSIONS

When using ALP to produce germinants for sowing ex vitro, it is preferable to ensure that the duration of in vitro culture is set to optimize both yield of germinants meeting criteria set for germinant selection as well as germinant survival and conversion. Although prolonging ALP can result in more germinants elongating such that they meet selection criteria, this can have a negative impact on the tolerance of germinants to the ex vitro environment as assessed by survival and conversion. In this trial, best germinant yields were obtained where ALP was 5 or more days in length following 7 days on semi-solid medium, and survival and conversion were highest for treatments where ALP was less than 8 days in length.

The invention claimed is:

1. A process of priming somatic germinants of loblolly pine or radiata pine, which comprises:
    fully immersing somatic germinants of loblolly pine or radiata pine in a sterile liquid nutrient medium to form a sterile liquid nutrient medium containing the germinants,
    bubbling an oxygen-containing gas through the sterile liquid nutrient medium containing the germinants to form an aerated germinant-containing nutrient medium,
    exposing the aerated germinant-containing nutrient medium to light,
    continuing said immersing, bubbling and exposing to light to produce at least some successfully primed and autotrophic germinants in a germinant-containing nutrient medium that are adapted for subsequent planting and converting to viable seedlings, and
    removing said successfully primed and autotrophic germinants from the aerated germinant-containing nutrient medium.

2. The process according to claim 1, wherein, if germinants that are unsuitable for planting and conversion to seedlings are present as well as said successfully primed and autotrophic germinants, said successfully primed and autotrophic germinants are separated from said unsuitable germinants and said unsuitable germinants are discarded.

3. The process of claim 1, wherein said immersion, bubbling and exposure to light are continued for up to 10 days.

4. The process of claim 1, wherein said immersion, bubbling and exposure to light is continued for 2 to 7 days.

5. The process of claim 1, wherein said exposure to light is carried out for 12 to 24 hours per day photoperiod.

6. The process of claim 1, wherein said exposure to light is carried out at a light intensity in the range of 5-200 $\mu molm^{-2} s^{-1}$ PPF.

7. The process of claim 6, wherein said exposure to light is carried out at a light intensity in the range of 20-50 $\mu molm^{-2} s^{-1}$ PPF.

8. The process of claim 1, wherein said oxygen-containing gas—is bubbling through the liquid nutrient medium at a rate to prevent the germinants from settling or layering.

9. The process of claim 1, wherein the rate of oxygen-containing gas bubbling through the liquid nutrient medium is in a range of 300-1500 ml/min.

10. The process of claim 1, wherein the rate of oxygen-containing gas bubbling through the liquid nutrient medium is in a range of 750-1500 ml/min.

11. The process of claim 1, wherein the temperature of the germinant-containing nutrient medium is maintained in the range of 25-35° C.

12. The process of claim 1, wherein said somatic germinants used in said process are produced by placing mature, desiccated somatic embryos of loblolly pine or radiata pine on an imbibition and germination medium to cause imbibition and subsequent germination of said embryos.

13. A process of priming somatic germinants of loblolly pine or radiata pine, which comprises:
    fully immersing somatic germinants of loblolly pine or radiata pine in a sterile liquid nutrient medium in a vessel to form a sterile liquid nutrient medium containing the germinants,
    bubbling an oxygen-containing gas through the sterile liquid nutrient medium containing the germinants to form an aerated germinant-containing nutrient medium,
    exposing the aerated germinant-containing nutrient medium to light,
    continuing said immersing, bubbling and exposing to light to produce at least some successfully primed and autotrophic germinants in the aerated germinant-containing nutrient medium that are adapted for subsequent planting and conversion to viable seedlings, and
    removing said successfully primed and autotrophic germinants from the aerated germinant-containing nutrient medium,
    wherein said removal of primed and autotrophic germinants for selection of said germinants suitable for sowing is facilitated by allowing said vessel to stand unagitated until fractionation occurs, optionally adding water or aqueous solution to the aerated germinant-containing nutrient medium, and then decanting the top fraction containing a majority of primed and autotrophic germinants suitable for sowing ex vitro.

14. The process of claim 1, wherein said germinants are of loblolly pine.

15. The process of claim 1, wherein said germinants are of radiata pine.

16. A process of priming somatic germinants of loblolly pine or radiata pine, which comprises:
    fully immersing somatic germinants of loblolly pine or radiata pine in a sterile liquid nutrient medium,
    bubbling an oxygen-containing gas through the sterile liquid nutrient medium containing the germinants to form an aerated germinant-containing nutrient medium,
    exposing the aerated germinant-containing nutrient medium to light,
    continuing said immersing, bubbling and exposing to light for a period of time from 1 to 14 days to produce at least some successfully primed and autotrophic germinants that are adapted for subsequent planting and conversion to viable seedlings, and
    removing said successfully primed and autotrophic germinants from the aerated germinant-containing nutrient medium.

17. The process of claim 16, wherein said somatic germinants are of loblolly pine.

18. The process of claim 16, wherein said somatic germinants are of radiata pine.

19. A process of priming somatic germinants of loblolly pine or radiata pine, which comprises:
    fully immersing somatic germinants of loblolly pine or radiata pine in a sterile liquid nutrient medium to form a sterile liquid nutrient medium containing the germinants,
    bubbling an oxygen-containing gas through the sterile liquid nutrient medium containing the germinants to form an aerated germinant-containing nutrient medium,
    continuing said immersing and bubbling to produce at least some successfully primed autotrophic germinants in the aerated germinant-containing nutrient medium that are adapted for subsequent planting and conversion to viable seedlings, and
    removing said successfully primed autotrophic germinants from the aerated germinant-containing nutrient medium.

20. The process of claim 1, wherein said successfully primed autotrophic germinants removed from said germinant-containing nutrient medium are transferred to a non-sterile greenhouse environment.

* * * * *